Dec. 10, 1957 R. DEROUX Plant Pat. 1,668
PEACH TREE
Filed May 21, 1957
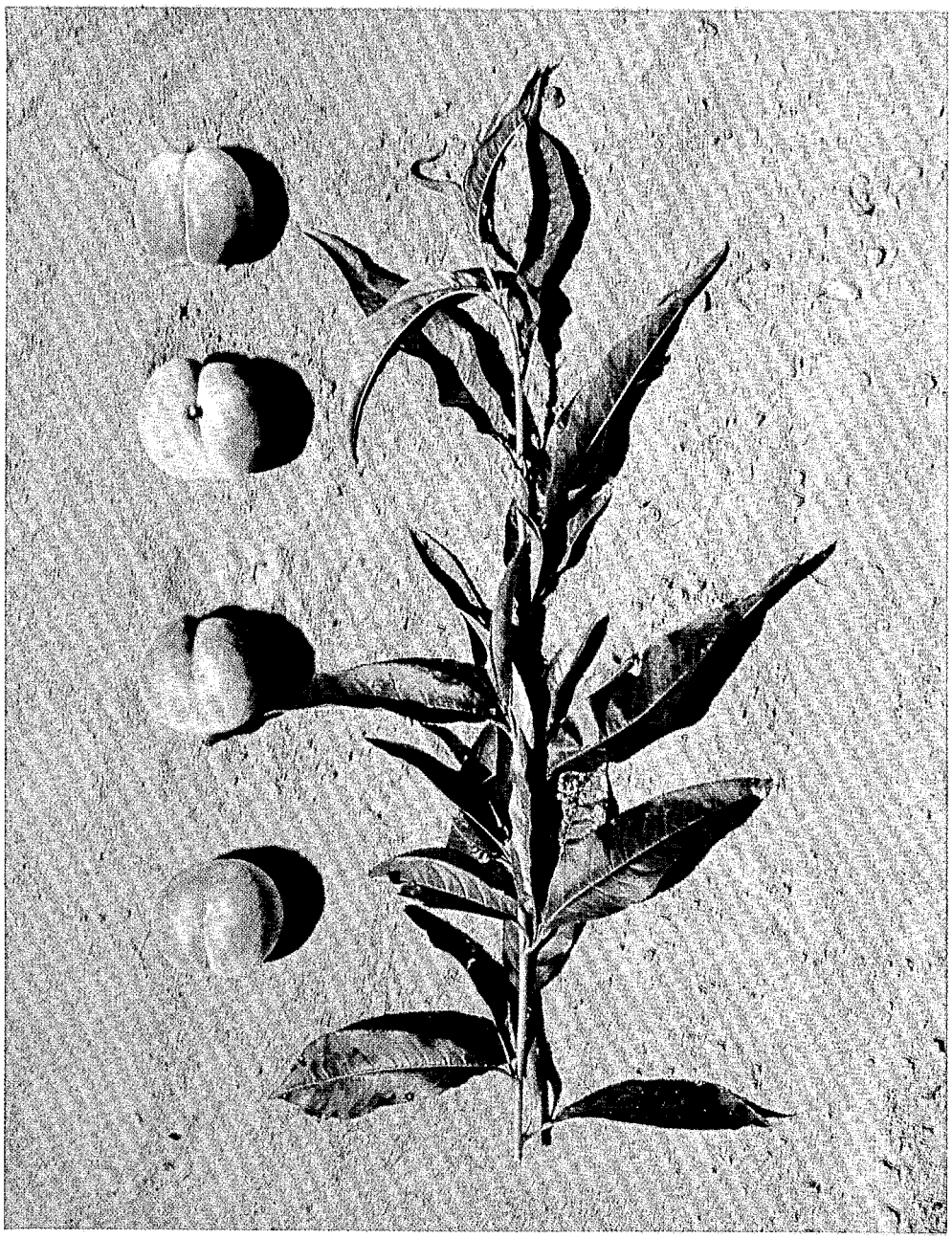
INVENTOR
Raymond Deroux
BY Robert Robb
ATTORNEYS United States Patent Office Plant Pat. 1,668
Patented Dec. 10, 1957

1,668

PEACH TREE

Raymond Deroux, Marges, France, assignor, by mesne assignments, to Stark Bro's Nurseries and Orchards Co., Louisiana, Mo., a corporation of Missouri Application May 21, 1957, Serial No. 660,729

Claims priority, application France June 29, 1956

1 Claim. (Cl. 47—62)

The present invention relates to a new and distinct variety of peach tree which was discovered by me as a bud sport of the variety known as "Mayflower" (unpatented), the discovery having been made in my cultivated orchard located at Marges (Drome), France.

While cultivating "Mayflower" peaches in my orchard referred to above, my attention was attracted to the unusually early ripening and greater coloration of the fruit on a limb of a "Mayflower" peach tree in contrast to the normal habits of the "Mayflower" variety, and I thereupon kept this limb under close observation. Continued observations and subsequent tests and asexual reproduction of the sport aforesaid fully established and confirmed that the early ripening habit and the greater coloration of the fruit of the sport were fixed and come true to form by asexual reproduction.

The tests and observations also established additional important characteristics of the new sport which distinguish it from its parent, "Mayflower," and which, when considered together, represent a new and improved combination of the following features:

(1) Early ripening habit as compared to "Mayflower" which heretofore has been the earliest peach on the French market—from 8 to 10 days earlier;

(2) More coloration of the fruit as compared with the fruit of "Mayflower";

(3) Greater productivity than "Mayflower";

(4) Less tendency of the stones to split when the fruit is ripe; and (5) Hardier flowers, and consequent greater cold resistance in the spring as compared with those of "Mayflower."

Asexual reproduction of my new variety by budding, as performed by me in my orchard at Marges (Drôme), France, shows that the foregoing characteristics come true to form and are established and transmissible through succeeding propagations, and definitely differentiate the new sport from its parent, as well as from all other peach varieties of which I am aware.

The accompanying drawing shows typical specimens of the fruit and foliage of my new variety as depicted in color.

The following is a detailed description of the new variety, with color terminology in accordance with general color terms of ordinary dictionary significance:

Observations made from specimens grown at Marges (Drôme), France.

Tree: Medium tall; vigorous; semi-erect; bushy; somewhat vase-formed; hardy; very productive; regular bearer; floral buds born even on suckers.

*Trunk.*—Medium stockiness. Bark—medium roughness; color—grey.

*Branches.*—Medium stockiness; medium roughness; many lenticels of medium size; seven nodes of floral buds of generally double form on the central 20 cm. section of the branch.

*Leaves.*—Lanceolate; pointed at apex; oval-pointed at base; medium size; medium thickness; smooth; slightly undulated near the petiole; semi-horizontally positioned towards the branch. Length (excluding petiole)—between maximum 14.5 cm. and minimum 11.0 cm.—average 12.3 cm. Width—between maximum 3.5 cm. and minimum 3.0 cm.—average 3.2 cm. Color:—upper side—moderately deep green, under side—slightly clearer and whiter; in autumn, the leaves become violet green, with the veins purple red on their under side. Margin—notched, with fine serrations. Petiole—rather short; sometimes of medium length, varying from 0.8 cm. to 1.1 cm. Glands—2 or 3 per leaf; generally 2, but seldom 4; alternate at the apex of the petiole or at the base of the leaf, and often on small lobes of the leaf; rather small; globular; not pubescent.

Flowers: Bloom in mid-season at about the same time as "Amsden" (unpatented) and "Mayflower" (unpatented); roseate type.

*Size.*—Rather large.

*Color.*—Rosy like "Mayflower."

Fruit:

*Date when described.*—June 13th.

*Size.*—Rather small; substantially same size as "Mayflower" fruit (about 12 to the kilo); substantially uniform in size and not as irregular as "Mayflower" fruit. Axial diameter—from 4.8 to 5.3 cm. Transverse diameter in suture plane—from 4.6 to 4.9 cm. Diameter at right angle to suture plane—from 5.1 to 5.8 cm.

*Form.*—Regular; slightly more spherical and more regular than "Mayflower"; slightly asymmetrical due to one lip being sometimes more developed than the other.

*Suture.*—Moderately visible, but still rather superficial (from 0.5 to 0.7 cm.); suture often prolonged beyond pistil point in more superficial manner, but divides fruit into two hemispheres; sometimes a slight depression around the pistil point.

*Pistil point.*—Slightly pointed and erect; does not go beyond the plane tangent to the apex of the fruit.

*Stem.*—Rather short (slightly shorter than "Mayflower").

*Cavity.*—Rounded or slightly elongated in the plane of the suture; dimensions slightly less than "Mayflower." Width—from 1.1 to 1.4 cm. Depth—from 0.5 to 0.7 cm.

*Skin.*—Semi-thin; separates well from the flesh; rather sparse and thin down. Color—deep yellow, lightly overcast with rose, with from one-half to two-thirds carmine red, shading to purple in the center of the carmine red zone; edge of latter zone is speckled carmine red, with a bit of yellow in the center.

*Flesh.*—Color—white or uniformly creamy-white; sometimes slight marks of rose red under the skin and also around some of the stone cavities. Texture—rather tender; with grains of medium size. Juice—abundant. Fibres—rather few; tender. Ripens—usually begins near the most developed part. Flavor—slightly acid. Aroma—good fragrance and medium sweet—average slightly more than "Mayflower."

Stone: Semi-free.

*Size.*—Rather small. Length—about 2.4 cm. Width—about 1.9 cm. Thickness—about 1.5 cm.

*Fibres.*—Medium length.

*Base.*—Slightly oblique.

*Apex.*—Acuminate.

*Sides.*—Equal; curved.

*Surface.*—Irregularly furrowed, especially near the apex.

*Pits.*—Circular.

*Ridges.*—Elongated or angular.

*Ventral edge.*—Moderately thick; with wing towards center.

*Dorsal edge.*—Less marked than ventral edge; with small interrupted lateral ridges.

*Tendency to split.*—Very slight.

*Color.*—Bright yellowish beige.

Disease resistance: Good resistance to leaf-curl and medium resistance to coryneum as compared with other varieties grown under comparable cultural conditions at Marges (Drome), France.

Use: Dessert; local and regional markets; export markets.

Keeping quality: Good.

Shipping quality: Good.

I claim:

A new and distinct variety of peach tree of the semi-free stone and white-fleshed fruit type, substantially as herein shown and described, characterized particularly as to novelty by the earlier ripening habit, greater coloration and more rarely split stones of its fruit, its greater productivity, and its hardier flowers and their consequent greater resistance to spring freezes, all as compared with the variety "Mayflower" (unpatented).

No references cited.